US006911017B2

(12) United States Patent
Lee et al.

(10) Patent No.: US 6,911,017 B2
(45) Date of Patent: Jun. 28, 2005

(54) MRI VISIBLE CATHETER BALLOON

(75) Inventors: Jeong S. Lee, Diamond Bar, CA (US); Edwin Wang, Tustin, CA (US); Roseminda J. White, Wildomar, CA (US); Jose A. Romero, Perris, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 251 days.

(21) Appl. No.: 09/957,354

(22) Filed: Sep. 19, 2001

(65) Prior Publication Data

US 2003/0055449 A1 Mar. 20, 2003

(51) Int. Cl.$^7$ ............................................. A61M 29/00
(52) U.S. Cl. ................................. 604/96.01; 606/194
(58) Field of Search ................... 606/28, 192, 194; 604/96, 264; 600/420, 423, 433

(56) References Cited

U.S. PATENT DOCUMENTS

| 3,847,157 A | | 11/1974 | Caillouette et al. ......... 128/348 |
| 4,202,346 A | | 5/1980 | Granier ...................... 128/658 |
| 4,657,024 A | | 4/1987 | Coneys ....................... 128/658 |
| 4,778,455 A | | 10/1988 | Kousai et al. .............. 604/270 |
| 4,927,413 A | * | 5/1990 | Hess ......................... 604/96.01 |
| 4,989,608 A | | 2/1991 | Ratner ........................ 128/653 |
| 4,994,032 A | * | 2/1991 | Sugiyama et al. ...... 604/103.09 |
| 5,035,694 A | | 7/1991 | Kasprzyk et al. ............. 606/27 |
| 5,045,072 A | | 9/1991 | Castillo et al. ............. 604/280 |
| 5,087,256 A | | 2/1992 | Taylor et al. ................. 606/28 |
| 5,154,179 A | * | 10/1992 | Ratner ........................ 600/420 |
| 5,211,166 A | | 5/1993 | Sepponen ................ 128/653.6 |
| 5,464,023 A | * | 11/1995 | Viera ......................... 600/585 |
| 5,499,980 A | | 3/1996 | Euteneuer .................... 606/28 |
| 5,669,879 A | | 9/1997 | Duer ........................... 604/96 |
| 5,728,079 A | | 3/1998 | Weber et al. ............... 604/280 |
| 5,807,279 A | * | 9/1998 | Viera ......................... 600/585 |
| 5,817,017 A | | 10/1998 | Young et al. ............... 600/433 |
| 5,908,410 A | | 6/1999 | Weber et al. ............... 604/280 |
| 5,958,372 A | | 9/1999 | Ladd | |
| 5,964,705 A | | 10/1999 | Truwit et al. ............... 600/423 |
| 6,463,317 B1 | * | 10/2002 | Kucharczyk et al. ....... 600/411 |
| 6,574,497 B1 | | 6/2003 | Pacetti | |
| 6,628,980 B2 | * | 9/2003 | Atalar et al. ............... 600/423 |

FOREIGN PATENT DOCUMENTS

| EP | 0 016 057 B1 | 5/1979 |
| EP | 0 033 659 A2 | 2/1981 |
| EP | 0 165 742 A2 | 6/1985 |
| EP | 0 701 836 | 3/1996 |
| EP | 0 775 500 | 5/1997 |
| JP | 60-55964 | 9/1983 |
| WO | WO 80/00061 | 1/1980 |
| WO | WO 82/00413 | 2/1982 |
| WO | WO 95/14501 | 6/1995 |
| WO | WO 99/60920 | 12/1999 |
| WO | WO 01/64278 | 9/2001 |

OTHER PUBLICATIONS

Bibliographic Data.
Rubin et al., "Magnetic Susceptibility Effects and Their Application in the Development of New Ferromagnetic Catheters for Magnetic Resonance Imaging" Investigative Radiology, 25(12):1325–1332 (Dec. 1990).

* cited by examiner

Primary Examiner—Julian W. Woo
Assistant Examiner—Nguyen Victor
(74) Attorney, Agent, or Firm—Fulwider, Patton, Lee & Utecht LLP

(57) ABSTRACT

Medical devices or components thereof, and particularly intracorporeal devices for therapeutic or diagnostic uses, which are formed at least in part of a polymeric material and a ferromagnetic or paramagnetic material, so that the medical device or component thereof is visible on magnetic resonance imaging (MRI) scans. In one embodiment, the medical device is a balloon catheter having an MRI visible balloon. In a presently preferred embodiment, there is an insufficient amount of the ferromagnetic or paramagnetic material within a wall of the balloon or coated onto a wall of the balloon to make the balloon radiopaque.

21 Claims, 2 Drawing Sheets

MRI VISIBLE CATHETER BALLOON

BACKGROUND OF THE INVENTION

This invention generally relates to medical devices, and particularly to intracorporeal devices for therapeutic or diagnostic uses such as balloon catheters, and vascular grafts.

In percutaneous transluminal coronary angioplasty (PTCA) procedures, a guiding catheter is advanced until the distal tip of the guiding catheter is seated in the ostium of a desired coronary artery. A guidewire, positioned within an inner lumen of a dilatation catheter, is first advanced out of the distal end of the guiding catheter into the patient's coronary artery until the distal end of the guidewire crosses a lesion to be dilated. Then the dilatation catheter having an inflatable balloon on the distal portion thereof is advanced into the patient's coronary anatomy, over the previously introduced guidewire, until the balloon of the dilatation catheter is properly positioned across the lesion. Once properly positioned, the dilatation balloon is inflated with fluid one or more times to a predetermined size at relatively high pressures (e.g. greater than 8 atmospheres) so that the stenosis is compressed against the arterial wall and the wall expanded to open up the passageway. Generally, the inflated diameter of the balloon is approximately the same diameter as the native diameter of the body lumen being dilated so as to complete the dilatation but not overexpand the artery wall. Substantial, uncontrolled expansion of the balloon against the vessel wall can cause trauma to the vessel wall. After the balloon is finally deflated, blood flow resumes through the dilated artery and the dilatation catheter can be removed therefrom.

In such angioplasty procedures, there may be restenosis of the artery, i.e. reformation of the arterial blockage, which necessitates either another angioplasty procedure, or some other method of repairing or strengthening the dilated area. To reduce the restenosis rate and to strengthen the dilated area, physicians frequently implant a stent inside the artery at the site of the lesion. Stents may also be used to repair vessels having an intimal flap or dissection or to generally strengthen a weakened section of a vessel. Stents are usually delivered to a desired location within a coronary artery in a contracted condition on a balloon of a catheter which is similar in many respects to a balloon angioplasty catheter, and expanded to a larger diameter by expansion of the balloon. The balloon is deflated to remove the catheter and the stent left in place within the artery at the site of the dilated lesion. Stent covers on an inner or an outer surface of the stent have been used in, for example, the treatment of pseudo-aneurysms and perforated arteries, and to prevent prolapse of plaque. Similarly, vascular grafts comprising cylindrical tubes made from tissue or synthetic materials such as polyester, expanded polytetrafluoroethylene, and DACRON may be implanted in vessels to strengthen or repair the vessel, or used in an anastomosis procedure to connect vessels segments together.

To facilitate placement of the catheter at the desired location in the patient's vasculature, X-ray opaque (i.e., radiopaque) material is generally provided on conventional angioplasty catheters so that the physician can view the catheter under fluoroscopy. The radiopaque material is typically a metal marker band on the catheter shaft. For example, two marker bands on the inner tubular member of the shaft are typically provided, to indicate the proximal end and distal end of the working length of the balloon. Blending radiopaque material into the polymer matrix of the catheter components has been suggested as an alternative to radiopaque marker bands on the catheter shaft. Additionally, catheters visible to magnetic resonance imaging (MRI), also known as nuclear magnetic resonance (NMR) imaging systems have been suggested for use during MRI scans of a patient. MRI scans are used provide two-dimensional sectional images of a patient's internal body structures without exposing the patient to harmful radiation.

It would be a significant advance to provide catheter balloon or other medical device or component thereof with improved visibility within the patient.

SUMMARY OF THE INVENTION

This invention is directed to medical devices or components thereof, and particularly intracorporeal devices for therapeutic or diagnostic uses, which are formed at least in part of a polymeric material and a ferromagnetic or paramagnetic material, so that the medical device or component thereof is visible on magnetic resonance imaging (MRI) scans. In one embodiment, the medical device is a balloon catheter having an MRI visible balloon. While discussed below primarily in terms of a catheter balloon, it should be understood that the invention includes additional MRI visible medical devices or components thereof, and particularly expandable or inflatable members.

In a presently preferred embodiment, the MRI visible material is a ferromagnetic material, and a presently preferred ferromagnetic material is iron oxide, due to the ease of compounding iron oxide in the polymeric balloon material, the relative ease of dispersing in many types of balloon materials, and the lack of a magnetic field orientation effect in which the MRI image varies depending on the orientation of the medical device or component thereof. Preferably, a background is provided by a contrast solution within and/or around the balloon, such as the MRI visible bright/white background of a Gadolinium solution, to facilitate viewing the ferromagnetic containing balloon. A balloon with iron oxide present in the balloon wall in a concentration of about 5% is readily visible as a dark image in a bright background of a 1:10 Gadolinium contrast solution. A variety of suitable ferromagnetic materials can be used including iron, nickel and cobalt, and compounds thereof such as iron oxide, typically in the form of a fine powder. In one embodiment, the preferred MRI visible materials have hydrating power (i.e., they are present in a hydrated state), which facilitates MRI visibility. For example, in one embodiment, a proton donating fluid at the device or component is not required in order to produce the MRI image. In an alternative embodiment, the MRI visible material may be a paramagnetic material, preferably provided that magnetic field orientation effects are minimal or nonexistent. In one embodiment, the paramagnetic material is selected from the group consisting of dysprosium, gadolinium, chromium, copper, manganese, and vanadium, and compounds thereof such as dysprosium oxide.

The MRI visible materials suitable for use in the invention may be radiopaque in addition to being MRI visible. However, in a presently preferred embodiment, there is an insufficient amount of the ferromagnetic or paramagnetic material in or on the balloon wall to make the balloon radiopaque. The ferromagnetic or paramagnetic material does not have a disadvantageous effect on the strength and compliance of the balloon, unlike prior art catheter balloons in which it was proposed to make the balloon radiopaque by forming the balloon of a blend of polymeric and radiopaque materials. Specifically, such prior art catheter balloons would require a relatively large amount of radiopaque material to make the balloon radiopaque, which would consequently reduce the strength and effect the compliance of the balloon. Thus, the balloon of the invention, unlike prior art balloons, has an amount of ferromagnetic or paramagnetic material which is sufficient to make the balloon MRI visible but insufficient to make the balloon radiopaque, and does not have a radiopaque material (either the ferromagnetic or paramagnetic material, or a separate radiopaque material) in sufficient amounts to make the balloon radiopaque. Consequently, the balloon is MRI visible and is not radiopaque in use, and the balloon has excellent performance characteristics such as a relatively high rupture pressure.

The MRI visible ferromagnetic or paramagnetic material is a solid, typically with a particle size of about 0.01 to about 50 µm. In one embodiment of the invention, the ferromagnetic or paramagnetic material is dispersed in the polymeric material, preferably by compounding the polymeric material with the ferromagnetic or paramagnetic material. The term compounding should be understood to refer to a process in which a high concentration of ingredient(s) is mixed with a specific polymer to form a master batch. This master batch is then added to resin during extrusion to obtain a uniform dispersion of a desired concentration. As a result, the ferromagnetic material is typically located uniformly throughout the polymeric wall of the balloon as discrete particles of material. Alternatively, in another embodiment, the ferromagnetic or paramagnetic material is a coating on a surface of the polymeric wall of the balloon. The balloon may be a single layered balloon, or alternatively, may comprise multiple layers, at least one of which has the ferromagnetic or paramagnetic material therein or thereon. The multiple layers are preferably coextruded, although they may alternatively be separately extruded and then placed together. In one embodiment, the balloon has a first polymeric layer, and a second polymeric layer coextruded with the first layer and containing the ferromagnetic or paramagnetic material therein. In one embodiment, the second layer is an inner layer, to minimize any microbiological or other effects of the ferromagnetic or paramagnetic material on the patient.

The balloon may be detectable when viewed by magnetic resonance imaging as a dark image or alternatively as a bright image, depending on the nature of the MRI visible material forming the balloon. In a presently preferred embodiment, the MRI visible layer extends the entire length of the balloon. However, the ferromagnetic or paramagnetic material may be present in sections of the balloon covering less than the entire area of the balloon, including sections spaced apart along the length or around the circumference of the balloon.

In a presently preferred embodiment, the MRI visible medical device or component thereof is configured to be expandable or inflatable. It is particularly important to avoid disadvantageous effects on the strength of expandable or inflatable members, such as catheter balloons and vascular grafts, because the members are required to not tear or burst during expansion thereof. Thus, the relatively low loading of ferromagnetic or paramagnetic material, in accordance with the invention, is particularly advantageous in expandable or inflatable members.

The medical device or component thereof may comprise a variety of devices, including a vascular graft, a stent cover, and an intravascular catheter component, for a variety of clinical applications including coronary, peripheral, and neurological applications. Stent covers and vascular grafts of the invention generally comprise a tubular body formed at least in part of polymeric material and the ferromagnetic or paramagnetic material. The terminology vascular graft as used herein should be understood to include grafts and endoluminal prostheses which are surgically attached to vessels in procedures such as vascular bypass or anastomosis, or which are implanted within vessels, as for example in aneurysm repair or at the site of a balloon angioplasty or stent deployment. A balloon catheter of the invention, such as an angioplasty dilatation catheter or a stent delivery catheter, generally comprises an elongated shaft with at least one lumen and balloon on a distal shaft section with an interior in fluid communication with the at least one lumen. A wall of the catheter balloon, or a separate sheath member on an outer surface of the balloon, may be MRI visible in accordance with the invention.

The balloon, or other medical device or component thereof, of the invention has improved MRI visibility due to the ferromagnetic or paramagnetic material, without a disadvantageous effect on strength or compliance of the balloon. Additionally, radiopaque marker bands are not required on the balloon catheter of the invention for visualization of the balloon location in the patient. As a result, the distal section of the balloon catheter is more flexible and has a smaller profile for improved tracking compared to conventional balloon catheters. These and other advantages of the invention will become more apparent from the following detailed description when taken in conjunction with the accompanying exemplary drawings.

DETAILED DESCRIPTION OF THE INVENTION

Figure 1:
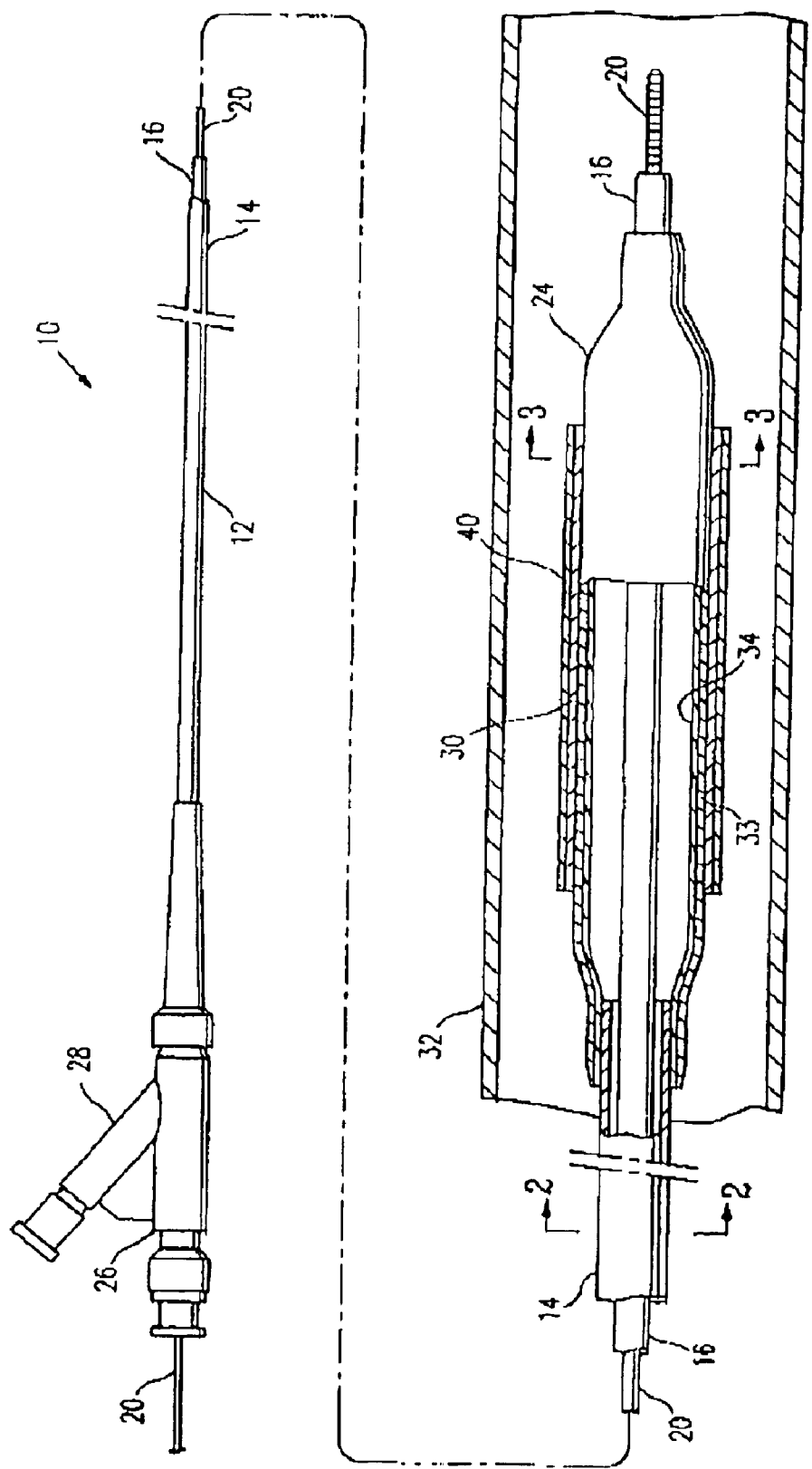
FIG. 1 is an elevational view, partially in section, of a stent delivery balloon catheter having a covered stent on the catheter balloon, which embodies features of the invention.
Figure 3:
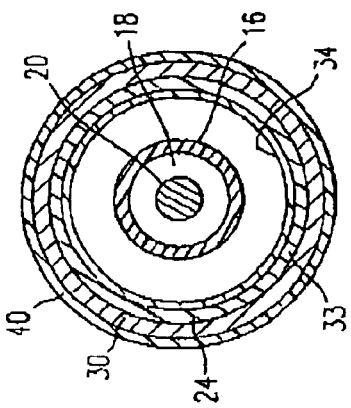
FIG. 3 is a transverse cross-section of the catheter shown in FIG. 1 taken at line 3—3, showing the covered stent disposed over the inflatable balloon.
Figure 2:
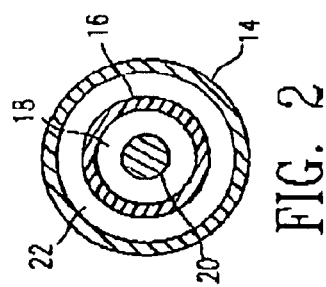
FIG. 2 is a transverse cross-section of the catheter shown in FIG. 1 taken at line 2—2.

FIGS. 1–3 illustrate an over-the-wire type stent delivery balloon catheter 10 embodying features of the invention. Catheter 10 generally comprises an elongated catheter shaft 12 having an outer tubular member 14 and an inner tubular member 16. Inner tubular member 16 defines a guidewire lumen 18 adapted to slidingly receive a guidewire 20, and the coaxial relationship between outer tubular member 14 and inner tubular member 16 defines annular inflation lumen 22 (see FIGS. 2 and 3, illustrating transverse cross sections of the catheter 10 of FIG. 1, taken along lines 2—2 and 3—3 respectively). An inflatable balloon 24 is disposed on a distal section of catheter shaft 12. Balloon 24 has a proximal shaft section sealingly secured to the distal end of outer tubular member 14 and a distal shaft section sealingly secured to the distal end of inner tubular member 16, so that its interior is in fluid communication with inflation lumen 22. An adapter 26 at the proximal end of catheter shaft 12 is configured to provide access to guidewire lumen 18, and to direct inflation fluid through arm 28 into inflation lumen 22. Balloon 24 has an inflatable working length located between tapered sections of the balloon. An expandable stent 30 is mounted on the balloon working length, with a stent cover 40 on an outer surface of the stent 30. FIG. 1 illustrates the balloon 24 in an uninflated configuration prior to deployment of the stent 30. The distal end of the catheter may be advanced in a conventional manner to a desired region of a patient's vessel 32 defining a body lumen, and balloon 24 inflated to expand stent 30, thereby implanting the stent in the body lumen.

The balloon 24 is formed of a polymeric material and an amount of ferromagnetic or paramagnetic material which is sufficient to make the balloon MRI visible and insufficient to make the balloon radiopaque within the patient. The ferromagnetic or paramagnetic material is preferably dispersed in the polymeric material forming the balloon wall, and in a presently preferred embodiment, the dispersed material is a ferromagnetic material. In the embodiment illustrated in FIG. 1, the balloon comprises an outer layer 33 and an inner layer 34, at least one of which is formed of the polymeric material/ferromagnetic or paramagnetic dispersion. The outer and inner layers 33/34 may be formed of the same polymeric material or different polymeric materials. A variety of suitable polymeric materials may be used to form the balloon, conventional in medical device balloon construction, including polyamides such as nylon 11 or nylon 12, copolyamides such as polyether block amide (PEBAX), copolyesters such as HYTREL or ARNITEL.

In a presently preferred embodiment, the amount of ferromagnetic or paramagnetic material is about 1% to about 30%, preferably about 5% to about 20%, by weight of the polymeric material/ferromagnetic or paramagnetic material dispersion, depending on the magnetic field strength, gradient field strength, and pulse sequences of the MRI system being used, as well as the clinical application of the catheter. The preferred percentages are for a multilayered balloon with a first layer formed of the MRI visible material dispersed in a polymer (i.e., the MRI visible layer), and a second layer free of the ferromagnetic or paramagnetic material. In an alternative embodiment in which the balloon is a single layered balloon (not shown) formed of the MRI visible material dispersed in a polymer, the concentration of ferromagnetic or paramagnetic material is typically lower, as for example about 50% lower than the above values for a single layered balloon having a wall thickness about 50% greater than the wall thickness of the MRI visible layer of the multilayered balloon. Applied as a coating, the ferromagnetic or paramagnetic material is preferably about 10% to about 20% or more by weight of the balloon.

The balloon 24 has a rupture pressure of about 200 to about 390 psi, preferably about 270 to about 330 psi. The rupture pressure is preferably the same as the rupture pressure of a balloon otherwise identical to the balloon but without the ferromagnetic or paramagnetic material.

The balloon catheter 10 can be used, for example in a balloon angioplasty procedure or stent deployment to treat a stenosed region of the patient's vasculature. The catheter 10 is introduced into the vessel 32 defining the body lumen, and advanced therein. The balloon is visualized under MRI to position the balloon at the desired location in the body lumen. The balloon is then inflated by introduction of inflation fluid into the balloon interior via the inflation lumen. A contrast solution is typically introduced into the balloon which doubles as the inflation fluid, and around the balloon through the guiding catheter, to enhance visibility of the balloon. A presently preferred contrast solution for a ferromagnetic containing balloon is a paramagnetic containing contrast solution. Because the wall of the balloon can be visualized during inflation thereof, the balloon 24 can be inflated at the site of a lesion in the body lumen to determine information about the lesion as part of a MRI diagnostic procedure. Specifically, for example, the compliance of the lesion to the inflated balloon can be determine by observing the balloon inflate against the lesion. Following the procedure, the balloon is deflated, and the catheter repositioned or removed from the patient.

Co-extruded balloon tubing, formed of a 20 wt % dispersion of iron oxide in a PEBAX 72D or Nylon 12 polymeric material as the inner layer of the multilayered balloon with a PEBAX 72D outer layer, was blow molded to form a balloon. The iron oxide particles had a particle size of about 0.01 $\mu$m. The balloon had a dual wall thickness of about 40 $\mu$m, and a burst pressure of about 250 psi to about 300 psi. The balloon was inflated at an inflation pressure of about 116 psi to about 150 psi to an inflated diameter of 3 mm, and MRI images of the inflated balloon were obtained at a field strength of 1.5 Tesla. A 1% to 10% Gadolinium solution in water is preferably used as a contrast solution within and/or around the balloon to enhance the visibility of the iron oxide containing balloon.

To the extent not discussed herein, the various catheter components can be formed conventionally of materials commonly used in catheter construction. The balloon 24 is typically secured to the catheter shaft as is conventionally known by adhesive or fusion bonding.

The dimensions of catheter 10 are determined largely by the size of the guidewires to be employed and the size of the artery or other body lumen through which the catheter must pass or the size of the stent being delivered. The outer tubular member 14 typically has an inner diameter of about 0.015 to about 0.035 inch (0.038 to 0.089 cm), usually about 0.03 inch (0.076 cm). The inner tubular member 16 typically has an outer diameter of about 0.012 to about 0.016 inch (0.030 to 0.041 cm), usually about 0.014 inch (0.036 cm). The overall working length of the catheter 10 may range from about 100 to about 150 cm, and is typically about 135 cm. Preferably, balloon 24 has a length about 0.5 cm to about 6 cm and typically about 2 cm, and an inflated working diameter of about 1 to about 8 mm, typically about 3 mm.

Figure 5:
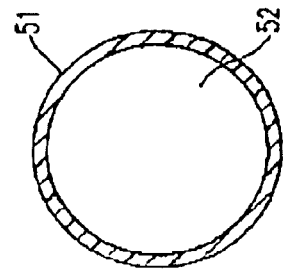
FIG. 5 is a transverse cross-section of the graft or cover shown in FIG. 4, taken along lines 5—5.
Figure 4:
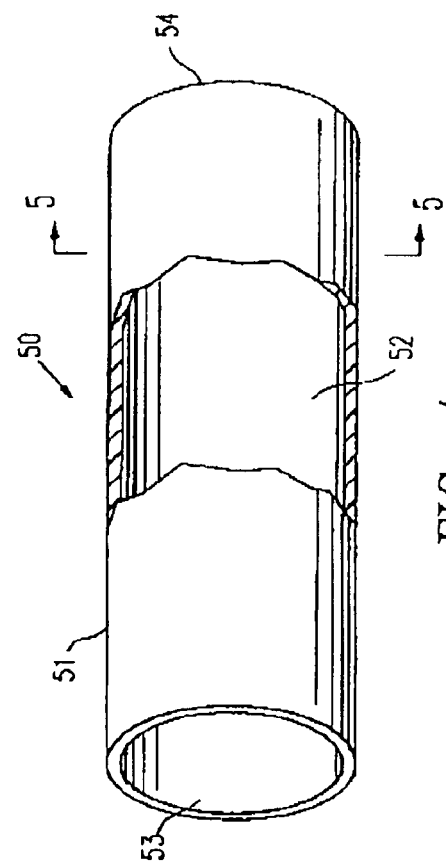
FIG. 4 is an elevational view, partially in section, of a vascular graft or stent cover which embodies features of the invention.

FIGS. 4 and 5 illustrate another embodiment of the invention, in which the expandable MRI visible medical device is a vascular graft 50. The vascular graft 50 generally comprises a tubular body 51 formed at least in part of a polymeric material and a ferromagnetic or paramagnetic material in accordance with the invention, having a lumen 52 therein and ports 53, 54 at either end of the graft 50. The graft 50 is configured for being implanted in the patient, and it may be expanded into place within a vessel, or surgically attached to a vessel such as to a free end or a side wall of a vessel. The graft 50 length is generally about 4 to about 80 mm, and more specifically about 10 to about 50 mm, depending on the application, and single wall thickness is typically about 40 $\mu$m to about 2000 $\mu$m, preferably about 100 $\mu$m to about 1000 $\mu$m. The diameter is generally about 1 to about 35 mm, preferably about 3 to about 12 mm, depending on the application. Stent cover 40 is similar to vascular graft 50, except it is on a stent as illustrated in FIG. 1.

While the present invention is described herein in terms of certain preferred embodiments, those skilled in the art will recognize that various modifications and improvements may be made to the invention without departing from the scope thereof. For example, in the embodiment illustrated in FIG. 1, the catheter is over-the-wire stent delivery catheter.

However, one of skill in the art will readily recognize that other types of intravascular catheters may be used, such as rapid exchange balloon catheters having a distal guidewire port and a proximal guidewire port and a short guidewire lumen extending between the proximal and distal guidewire ports in a distal section of the catheter. Additionally, although the balloon catheter illustrated in FIG. 1 is a stent deploying catheter, a variety of balloon catheters may be used including dilatation balloon catheters. Moreover, although individual features of one embodiment of the invention may be discussed herein or shown in the drawings of the one embodiment and not in other embodiments, it should be apparent that individual features of one embodiment may be combined with one or more features of another embodiment or features from a plurality of embodiments.

What is claimed is:

1. A balloon catheter, comprising:
   a) an elongated shaft, having a proximal end, a distal end, and at least one lumen within at least a section thereof; and
   b) a balloon on a distal shaft section, visible under magnetic resonance imaging, having a wall formed of a polymeric material and an amount of ferromagnetic or paramagnetic material dispersed in the polymeric material, the amount of ferromagnetic or paramagnetic material being about 1% to about 30% by weight of the dispersion and being sufficient to make the balloon visible under magnetic resonance imaging and insufficient to make the balloon radiopaque.

2. The balloon catheter of claim 1 wherein the material dispersed in the polymeric material is a ferromagnetic material.

3. The balloon catheter of claim 2 wherein the ferromagnetic material is iron oxide.

4. The catheter of claim 3 wherein the amount of iron oxide is about 5% to about 20% by weight of the dispersion.

5. The balloon catheter of claim 2 wherein the ferromagnetic material is selected from the group consisting of iron, nickel, chromium, cobalt, and compounds thereof.

6. The balloon catheter of claim 2 including a contrast solution in an interior of the balloon, the contrast solution having a paramagnetic material which appears bright under magnetic resonance imaging, so that the balloon appears dark in relation to the contrast solution under magnetic resonance imaging.

7. The balloon catheter of claim 1 wherein the paramagnetic material is selected from the group consisting of dysprosium, gadolinium, copper, manganese, vanadium, and compounds thereof.

8. The balloon catheter of claim 1 wherein the balloon has multiple layers, at least one of which comprises the polymeric and ferromagnetic or paramagnetic material dispersion.

9. The balloon catheter of claim 8 wherein the balloon comprises a first layer, and a second layer which is coextruded with the first layer and which is formed of the polymeric and ferromagnetic or paramagnetic material dispersion.

10. The balloon catheter of claim 9 wherein the second layer is an inner layer relative to the first layer.

11. The balloon catheter of claim 9 wherein the second layer is an outer layer relative to the first layer.

12. A balloon catheter, comprising:
   a) an elongated shaft, having a proximal end, a distal end, and at least one lumen within at least a section thereof; and
   b) a balloon visible under magnetic resonance imaging, having a wall formed of a dispersion of a polymeric material and an amount of ferromagnetic material, the amount of ferromagnetic material being about 5% to about 20% by weight of the dispersion and being sufficient to make the balloon visible under magnetic resonance imaging and insufficient to make the balloon radiopaque.

13. The balloon catheter of claim 12 wherein the balloon is a single layered balloon.

14. The balloon catheter of claim 12 wherein the balloon comprises a first layer, and a second layer which is coextruded with the first layer and which is formed of the polymeric material and ferromagnetic material dispersion.

15. The balloon catheter of claim 12 wherein the ferromagnetic material is iron oxide.

16. A balloon catheter, comprising:
   a) an elongated shaft, having a proximal end, a distal end, and at least one lumen within at least a section thereof; and
   b) a balloon on a distal shaft section, visible under magnetic resonance imaging, having a wall formed of a polymeric material and an amount of ferromagnetic or paramagnetic material, the amount of ferromagnetic or paramagnetic material being not greater than about 30% by weight of the balloon and being sufficient to make the balloon visible under magnetic resonance imaging and insufficient to make the balloon radiopaque.

17. The balloon catheter of claim 16 wherein the ferromagnetic or paramagnetic material is dispersed in the polymeric material or coated onto a surface of the balloon formed of the polymeric material.

18. A balloon catheter, comprising:
   a) an elongated shaft, having a proximal end, a distal end, and at least one lumen within at least a section thereof; and
   b) a balloon on a distal shaft section, visible under magnetic resonance imaging, having polymeric wall formed of a polymeric material compounded with an amount of ferromagnetic or paramagnetic material so that the ferromagnetic or paramagnetic material is uniformly dispersed throughout the polymeric wall of the balloon, the amount of ferromagnetic or material being sufficient to make the balloon visible under magnetic resonance imaging nad insufficient to make the medical device or component thereof radiopaque and being about 1% to about 30% by weight of the dispersion.

19. The balloon catheter of claim 18 wherein the ferromagnetic or paramagnetic material has a particle size of about 0.01 to about 50 $\mu$m.

20. The balloon catheter of claim 18 wherein the ferromagnetic or paramagnetic material is finely divided.

21. A medical device or component thereof, configured to be expandable, and having a wall formed of a polymeric material and an amount of ferromagnetic or paramagnetic material dispersed in the polymeric material, the amount of ferromagnetic or paramagnetic material being about 1% to about 30% by weight of the dispersion and being sufficient to make the medical device or component thereof visible under magnetic resonance imaging and insufficient to make the medical device or component thereof radiopaque.

* * * * *

UNITED STATES PATENT AND TRADEMARK OFFICE
CERTIFICATE OF CORRECTION

PATENT NO. : 6,911,017 B2
APPLICATION NO. : 09/957354
DATED : June 28, 2005
INVENTOR(S) : Jeong S. Lee et al.

It is certified that error appears in the above-identified patent and that said Letters Patent is hereby corrected as shown below:

Column 8, line 45, claim 18, insert --paramagnetic-- after "or".

Signed and Sealed this

Fifteenth Day of January, 2008

JON W. DUDAS
*Director of the United States Patent and Trademark Office*